United States Patent [19]

Cassaday et al.

[11] Patent Number: 5,149,658
[45] Date of Patent: Sep. 22, 1992

[54] METHOD FOR THE SEPARATION AND/OR FORMATION OF IMMISCIBLE LIQUID STREAMS

[75] Inventors: Michael M. Cassaday, Valhalla; Vito F. Christiano, Somers, both of N.Y.; Bachalli Vasudeva, Princeton Junction, N.J.

[73] Assignee: Technicon Instruments Corporation, Tarrytown, N.Y.

[21] Appl. No.: 628,804

[22] Filed: Dec. 14, 1990

Related U.S. Application Data

[62] Division of Ser. No. 73,049, Jul. 14, 1987.

[51] Int. Cl.$^5$ .............................................. G01N 35/08
[52] U.S. Cl. .......................................... 436/53; 422/82; 210/439; 210/441; 210/445; 210/449; 73/863.23; 73/863.58; 73/863.61; 73/863.71; 73/863.81
[58] Field of Search .................. 436/52, 53; 73/863.23, 73/863.58, 863.21, 863.51, 863.61, 863.71, 863.81; 422/82; 210/439, 441, 445, 446, 449

[56] References Cited

U.S. PATENT DOCUMENTS

| | | | |
|---|---|---|---|
| 2,926,527 | 3/1970 | Crandall | 73/863.58 |
| 3,640,822 | 2/1972 | Hrdina | 422/82 |
| 3,699,004 | 10/1972 | Skeggs | 436/53 |
| 3,743,103 | 7/1973 | Isreeli et al. | 422/82 |
| 3,784,902 | 1/1974 | Huber | 73/863.23 |
| 3,843,326 | 10/1974 | Lichtenstenen | 422/82 |
| 3,921,458 | 11/1975 | Logan | 73/863.58 |
| 4,091,835 | 5/1978 | Frampton | 73/863.58 |
| 4,167,117 | 9/1979 | Stokley et al. | 73/863.58 |
| 4,239,494 | 12/1980 | Clements | 422/82 |
| 4,253,846 | 3/1981 | Smythe et al. | 436/53 |
| 4,413,533 | 11/1983 | Diesel | 73/863.58 |
| 4,456,014 | 6/1984 | Buck et al. | 73/863.23 |
| 4,594,902 | 6/1986 | Compton et al. | 73/863.23 |
| 4,683,212 | 7/1987 | Uffenheimer | 436/52 |

Primary Examiner—Lynn M. Kummert
Attorney, Agent, or Firm—Jeffrey M. Greenman; James J. Romano, Jr.

[57] ABSTRACT

Apparatus and method are provided for the substantial separation on a continuous flow basis of immiscible liquids flowing as a common stream, with one of the liquids substantially encapsulating another of the liquids, in a flow conduit. The conduit comprises an inner surface which is selectively "wettable" by one of the liquids to the substantial exclusion of another of the liquids; and the liquid separator apparatus are disposed in the conduit and operate to substantially separate the liquids, or at least a portion of one of the liquids, from the common liquids stream as that stream flows into contact with the separator apparatus in the conduit.

Apparatus and method for the introduction of a liquid on a continuous flow basis into a flowing stream of another liquid which is immiscible therewith and is flowing in a flow conduit are also provided. The conduit again comprises an inner surface which is selectively "wettable" by one of the liquids to the substantial exclusion of the other of the liquids; and the liquid introduction apparatus are disposed in the conduit and operate to form a common stream of the liquids for continued flow in the conduit, with one of the liquids being substantially encapsulated by another of the liquids, as the liquids are merged at the liquid introduction apparatus in the conduit.

18 Claims, 7 Drawing Sheets

METHOD FOR THE SEPARATION AND/OR FORMATION OF IMMISCIBLE LIQUID STREAMS

This application is a division of co-pending application, Ser. No. 07/073,049, filed Jul. 14, 1987 by Messrs. Michael M. Cassaday, Vito F. Christiano and Bachalli Vasudeva, Ph.D.

BACKGROUND OF THE INVENTION

1. Field of the Invention

This invention relates to new and improved apparatus and method for the substantial separation and/or formation of immiscible liquid streams on a continuous flow basis; and which are particularly adapted to use in automated, continuous flow sample liquid analysis systems to maximize the accuracy of the sample liquid analysis results.

2. Description of the prior art

Although a number of methods and apparatus are known for the separation of sample liquids from immiscible isolation liquids within which the same are encapsulated for minimization of sample liquid carryover attendant sample liquid analysis, these will generally be found to rely primarily upon the natural separational effects of the differences in specific gravity between those liquids; and thus will not be found effective to accomplish the virtually immediate, and complete in terms of totally distinct locations of the thusly separated liquids, substantial separation of the liquids on a continuous flow basis as inherently provided by the apparatus and method of this invention.

More specifically U.S. Pat. No. 4,121,466 issued Oct. 24, 1978 to Allen Reickler, et al for "Liquid Dispenser With An Improved Probe" and assigned to the assignee hereof, discloses the use of an immiscible hydrophobic isolation liquid to encapsulate successive aqueous sample liquids for minimization of sample liquid carryover attendant sample liquid analysis. In this apparatus, wherein the isolation liquid is of greater density than the sample liquids, the former is simply allowed to settle out from the latter to the bottom of a reaction receptacle into which the isolation liquid-encapsulated sample liquids are dispensed, thereby leaving the sample liquid readily accessible for reaction with reagent liquids as may then be introduced into the receptacle. The settling out of the isolation liquid can and does take time and, in any event, leaves the thusly separated isolation and sample liquids in essentially the same location, e.g. the reaction receptacle.

In like manner, U.S. Pat. No. 4,357,301 issued Nov. 2, 1982 to Michael M. Cassaday, et al for "Reaction Cuvette" and assigned to the assignee hereof, also discloses the use of an immiscible isolation liquid to encapsulate successive aqueous sample liquids for minimization of sample liquid carryover attendant sample liquid analysis. In this apparatus wherein the isolation liquid is again hydrophobic and apparently of greater density than the sample liquids, sharp projections or the like of a hydrophilic material are provided at the bottom of the reaction cuvette, and operate to puncture the isolation liquid-encapsulated sample liquids as the same are introduced into the cuvette; thereby freeing for reaction the sample liquids from the isolation liquid which simply floats to the top of the cuvette. Again, this separation can and does take time, and in any event, leaves the isolation and sample liquids in essentially the same location, e.g. the reaction cuvette.

Under the circumstances, it has been determined by applicants that the continued presence of the "separated" isolation liquid with the sample liquid at the same location can and does present significant problems with regard to the accuracy of subsequent sample liquid analysis results; and especially in those instances wherein those sample liquid analysis results are arrived at through use of sample liquid analysis methodologies involving, for example, reflectance spectroscopy, ion selective electrodes, colorimetry, cell counting and or enzyme coil operation.

Hydrophobic filtration, for example as disclosed by the "nonwet" filter in U.S. Pat. No. 4,266,559 issued May 12, 1981 for David S. Akhavi for "Blood Sampler," wherein a filter of hydrophobic material is used to prevent the escape of an aqueous sample liquid from a collection device while permitting the passage of air therethrough to enable filling of the device, is also known in the prior art, but is clearly totally irrelevant to the substantial separation of immiscible liquids from a flowing stream to distinct locations on a continuous flow basis.

Also of limited relevance to liquid separation are conventional debubbler devices as have now become standard in continuous flow sample liquid analysis systems and which operate to remove the air segments from a continuously flowing, air segmented sample liquid stream prior to sample liquid analysis. These debubbler devices, which operate primarily on the very significant differences in specific gravity between air and the sample liquids of interest are clearly totally inapplicable to the effective substantial separation of immiscible liquids on a continuous flow basis.

With regard to immiscible liquid stream formation, it is known in the prior art to form immiscible liquid streams on a continuous flow basis by the essentially concomitant introduction of aqueous sample liquids, and a hydrophobic isolation liquid which is immiscible therewith, into a hydrophobic flow conduit which is selectively "wettable" by the isolation liquid to the substantial exclusion of the aqueous sample liquids, thereby essentially encapsulating the former in a layer of the latter and effectively minimizing aqueous sample liquid carryover.

More specifically, in most instances, this will be seen to be accomplished by the concomitant aspiration of the aqueous sample liquids and the immiscible isolation liquid into the sample analysis system by the sample aspirating probe as disclosed, for example, in U.S. Pat. No. 4,121,466 as discussed hereinabove, and in each of the U.S. Pat. No. 4,253,846 issued Mar. 3, 1981 to William J. Smythe, et al for "Method and Apparatus for Automated Analysis of Fluid Samples," and assigned to the assignee hereof, and U.S. Pat. No. 4,517,302 issued May 14, 1986 to Steven Saros, et al for "Sample Analysis System," and also assigned to the assignee hereof. Although prior art apparatus of this nature do operate to satisfactorily continuously form the isolation liquid layer-encapsulated, sample liquid stream, the same are of course limited in location to the aspirating probe at the entry point of the analysis system without the system flow conduit, thereby limiting the versatility thereof. In addition, since these prior art apparatus are strictly tied into the operation of the analysis system aspirating probe, satisfactory operation thereof by definition requires the use of moving parts which can prove somewhat problematical. Also, the extremely high speeds of operation of contemporary sample liquid analysis systems of the nature here under discussion require extremely high speeds of aspiration probe movement through decidedly limited distances, and these requirements can adversely affect the satisfactory formation of the isolation liquid layer by the probe.

U.S. Pat. No. 3,479,141 issued Nov. 18, 1969 to William J. Smythe, et al, and now expired, for "Method and Apparatus for Analysis," and assigned to the assignee hereof, discloses the formation on a continuous flow basis of an isolation liquid layer sample liquid stream by the concomitant pumping through separate compressible pump tubes of a peristaltic pump of immiscible isolation and buffer liquids to a tube junction for merger therein and flow therefrom through the recipient side of a dialyzer to acquire the sample liquids for subsequent flow of the thusly isolation liquid encapsulated sample liquid stream through a glass conduit to a hydrophobic conduit for additional sample liquid processing. Formation of the isolation liquid-encapsulated sample liquid stream in this manner of necessity results in an extremely "rich" isolation liquid layer, to very significant economic disadvantage as made clear by FIG. 1 of the drawing of that patent; and operates to effectively minimize sample liquid carryover only upon the arrival of the stream at the hydrophobic conduit. In addition, formation of the isolation liquid-encapsulated sample liquid stream in this manner is, of course, unduly complex, and simply cannot in any event provide the precision of isolation liquid layer formation as required by more contemporary, highly technically sophisticated continuous flow sample liquid analysis systems.

U.S. Pat. No. 3,726,297 issued Apr. 10, 1973 to Richard H. Heimann, Aaron Kassel and Donald F. Kopelman for "Method And Device For Introducing For Mixing A First Liquid Into A Second Liquid," and assigned to the assignee hereof, discloses a tube disposed within an elongated passageway in which a first liquid is flowing for introducing a second liquid thereinto for mixture with said first liquid. In this device, the first and second liquids are, of course, not immiscible; and the second liquid is introduced into the first liquid in the countercurrent direction relative to the flow of the latter Accordingly, it will be immediately clear to those skilled in this art that the device of U.S. Pat. No. 3,726,297 is totally inapplicable to the formation of an isolation liquid-encapsulated sample liquid stream from immiscible isolation and sample liquids in a conduit which is selectively "wettable" by the isolation liquid to the substantial exclusion of the sample liquid.

OBJECTS OF THE INVENTION

It is, accordingly, an object of our invention to provide new and improved apparatus and method for the substantial separation on a continuous flow basis of immiscible liquids which are flowing in a common stream in flow conduit means.

It is another object of our invention to provide new and improved apparatus and method as above which are operable to separate those liquids to a very high degree of separational efficiency.

It is another object of our invention to provide apparatus and method as above which are operable to effect the virtually immediate separation of the liquids from the flowing common liquids stream.

It is another object of our invention to provide apparatus and method as above which are operable to separate said liquids, or at least a significant portion of one of the liquids, to distinct and spaced locations without contact therebetween.

It is another object of our invention to provide apparatus and method operable as above wherein one of said immiscible liquids is substantially encapsulated within a layer of the other of said liquids in said common flowing stream.

It is another object of our invention to provide apparatus and method as above wherein one of said immiscible liquids is an aqueous liquid which is to be separated from the other of said liquids.

It is another object of our invention to provide apparatus and method as above which are particularly adapted to the separation of immiscible liquids on a continuous flow basis in an automated sample liquid analysis system wherein said conduit means are hydrophobic, one of said immiscible liquids is a sample liquid, and the other of said liquids is a hydrophobic isolation liquid which substantially encapsulates the same for minimization of sample liquid carryover in said sample liquid analysis system.

It is another object of our invention to provide apparatus and method for introducing one or more liquids on a continuous flow basis into a flowing stream of a liquid which is immiscible therewith to form a common flowing stream of said immiscible liquids.

It is another object of our invention to provide liquid introduction apparatus and method as above wherein the thusly formed common stream of said immiscible liquids will comprise a stream of one of said liquids substantially encapsulated within a layer of the other of said liquids.

It is another object of our invention to provide apparatus and method as above which are operable to precisely form said encapsulating liquid layer to a predetermined minimum thickness commensurate with the function thereof, thereby minimizing the amount of said encapsulating liquid required for such function.

It is another object of our invention to provide liquid introduction apparatus and method as above which are operable to provide a wide range of predeterminable thicknesses for said encapsulating liquid layer, and which enable the formation of that encapsulating liquid layer to a precisely predetermined, minimum effective thickness within that range to thereby minimize the required amount of said encapsulating liquid to significant economic advantage.

It is another object of our invention to provide liquid introduction apparatus and method as above wherein one of said immiscible liquids is an aqueous liquid which is to be substantially encapsulated in a layer of the other of said liquids.

It is another object of our invention to provide liquid introduction apparatus and method as above which are particularly adapted to the formation of an immiscible liquid stream on a continuous flow basis in hydrophobic flow conduit means of an automated sample liquid analysis system wherein one of said immiscible liquids is an aqueous sample liquid, and the other of said liquids is a hydrophobic isolation liquid which substantially encapsulates the same for minimization of sample liquid carryover in said sample liquid analysis system.

It is another object of our invention to provide liquid introduction and liquid separation apparatus and method as above which are, in each instance, of particularly simple and straightforward configuration and manner of operation.

It is another object of our invention to provide liquid introduction and liquid separation apparatus as above which, in each instance, essentially require no moving parts, and are thus basically maintenance-free.

It is another object of our invention to provide liquid introduction and liquid separation apparatus as above which, in each instance, require the use of only readily available, relatively inexpensive materials of proven effectiveness and dependability to the task at hand, and which thus may be fabricated at relatively low cost.

It is another object of our invention to provide liquid introduction and liquid separation apparatus and method as above which are not limited by configuration or manner of operation to particular locations within a liquid processing system with which the same may be utilized, and which thus exhibit significant versatility of application.

It is a further object of our invention to provide liquid introduction and liquid separation apparatus and method as above which are particularly adapted for combined use in a continuous flow, automated sample liquid analysis system to form an isolation liquid layer-encapsulated, air-segmented, successive sample liquid stream for the minimization of sample liquid carryover, and to subsequently separate said sample liquid stream, substantially in whole or in part, from said isolation liquid encapsulating layer to prevent interference thereof with sample liquid analysis; thereby, in both respects maximizing the accuracy of the sample liquid analysis results.

BRIEF DESCRIPTION OF THE DRAWINGS

The above and other significant objects and advantages of our invention are believed made clear by the following detailed description thereof taken in conjunction with the following drawings wherein.

SUMMARY OF THE INVENTION

Figure 1:
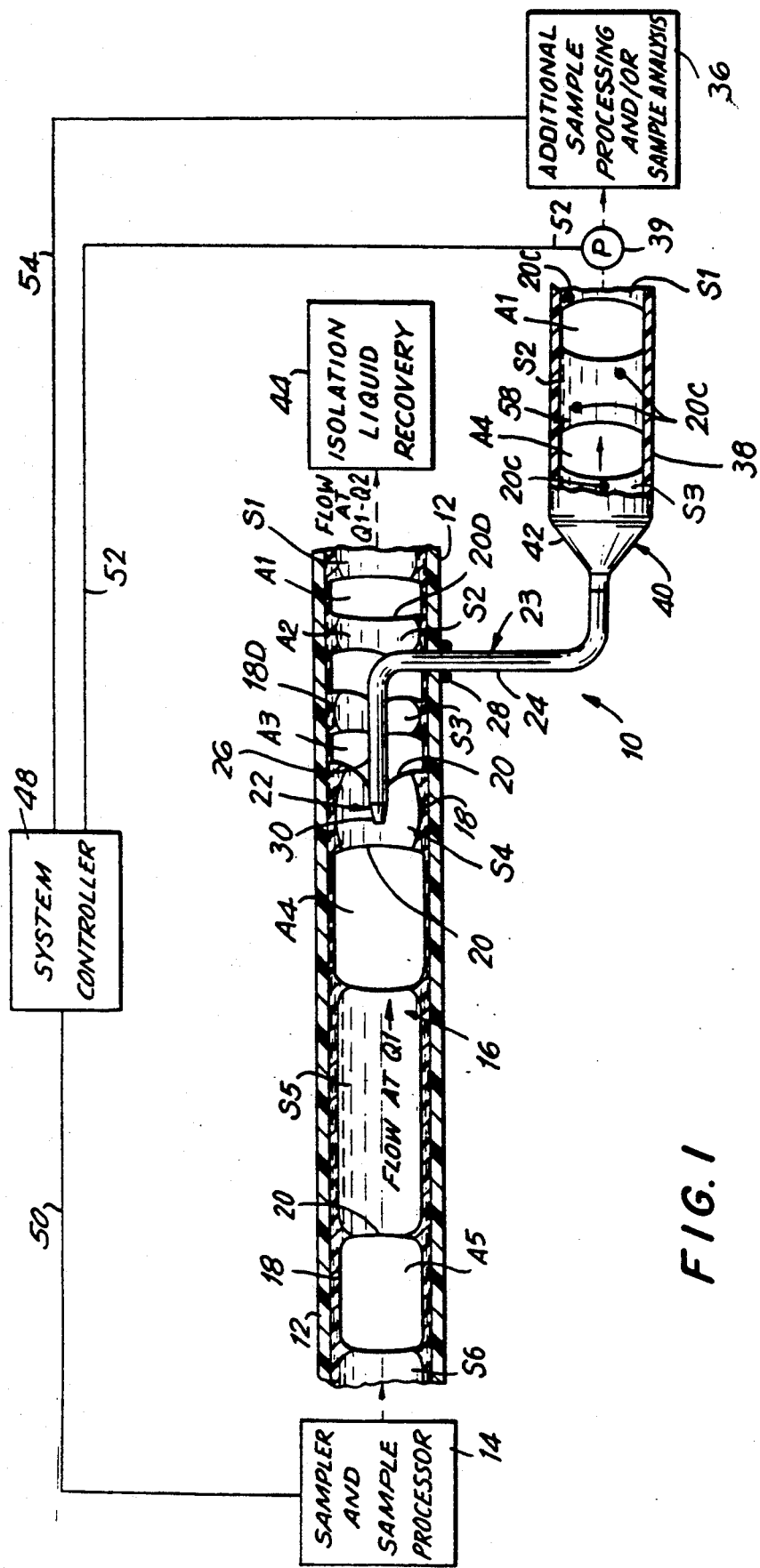
FIG. 1 is an essentially schematic diagram, with certain parts in cross-section, of a sample liquid analysis system including apparatus representatively configured and operable in accordance with the teachings of a first embodiment of our invention for substantially separating at least a portion of one or more liquids out of a flowing stream of immiscible liquids on a continuous flow basis.

As representatively disclosed herein in a first preferred embodiment, the immiscible liquid separating apparatus and method of our invention comprises probe means which are operatively associated with flow conduit means to continuously withdraw and thus separate an essentially central portion of an immiscible liquid stream flowing therethrough. The stream is formed by an air-segmented aqueous sample liquid stream which is substantially encapsulated in a layer of an immiscible hydrophobic isolation liquid which preferentially "wets" and is disposed at the hydrophobic inner conduit means surface to the substantial exclusion of the aqueous sample liquids which are flowing therewithin; thus insuring that the essentially central portion withdrawn by the probe means is substantially only aqueous sample liquid. The thusly substantially separated sample liquid stream portion is flowed by pump means from the probe means to secondary conduit means and therethrough to additional sample liquid processing and/or analysis means.

As representatively disclosed herein in a second preferred embodiment, the immiscible liquid separating apparatus and method of our invention comprise porous flow conduit insert means which are operatively associated with flow conduit means to continuously withdraw and thus separate the outer portion of an immiscible liquid stream flowing therethrough. This stream is formed by an air-segmented aqueous sample liquid stream which is substantially encapsulated in a layer of an immiscible hydrophobic isolation liquid which preferentially "wets" and is disposed at the inner conduit means and conduit insert means hydrophobic surfaces to the substantial exclusion of the aqueous sample liquids which are flowing therewithin; thus insuring that the outer stream portion withdrawn through the porous conduit insert means is substantially only the isolation liquid. Sleeve means are provided to surround the porous conduit insert means and provide a fluid-tight space therebetween, and pump means are operatively connected thereto to provide a differential pressure across the porous conduit insert means and promote the flow of the isolation liquid therethrough. The resultant, substantially isolation liquid-free sample liquid stream is flowed through the conduit means downstream of the porous conduit insert means to additional sample liquid processing and/or analysis means.

A representative combination in series in accordance with the teachings of our invention of the first and second preferred embodiments of the immiscible liquid separation apparatus and method of that invention in the same sample liquid analysis system for purposes of increase in the overall liquid separational efficiency is also disclosed.

As representatively disclosed herein in a third preferred embodiment, the liquid introduction apparatus and method of our invention comprise probe means which are operatively associated with flow conduit means to continuously introduce an air-segmented aqueous sample liquid stream into the essentially central portion of an immiscible hydrophic isolation liquid stream which is flowing in said conduit means, and which preferentially "wets" the hydrophobic inner surface of said conduit means to the substantial exclusion of the aqueous sample liquids. Introduction of the air-segmented sample liquid stream into the isolation liquid stream through the probe means displaces the latter stream to the inner conduit means surface for retention thereat in accordance with the preferential "wetting." This effectively forms a layer of the isolation liquid at the inner conduit means surface for encapsulation of the air-segmented, sample liquid stream and continued flow thereof through the flow conduit means to sample liquid processing and/or analysis means.

As representatively disclosed herein in a fourth preferred embodiment, the liquid introduction apparatus and method of our invention comprise porous flow conduit insert means which are operatively associated with flow conduit means to continuously introduce an immiscible hydrophobic isolation liquid into the outer portion of an air-segmented aqueous sample liquid stream which is flowing in said conduit means. This isolation liquid preferentially "wets" the inner hydrophobic surfaces of said flow conduit means and said conduit insert means to the substantial exclusion of the aqueous sample liquids; and thus effectively forms a layer of the isolation liquid at those inner surfaces for encapsulation of the air-segmented, sample liquid stream and continued flow thereof through the flow conduit means to sample liquid processing and/or analysis means.

A representative combination in series in accordance with the teachings of our invention of the liquid introduction apparatus and method thereof and the liquid separation apparatus and method thereof to in turn form the isolation liquid encapsulated air-segmented sample liquid stream and subsequently substantially separate the sample liquids, or at least significant portions thereof, from the isolation liquid, in the same sample liquid analysis system is also disclosed.

In each instance, it may be readily understood that the formation of the encapsulating isolation liquid layer is to minimize sample liquid carryover in the sample liquid analysis system, while the substantial separation of the sample liquids therefrom prior to additional sample liquid processing and/or analysis is to prevent interference by the isolation liquid with the performance of these functions. Thus, and in both events, the accuracy of the sample liquid analysis results is maximized to significant advantage by the apparatus and method of our invention.

DETAILED DESCRIPTION OF THE INVENTION

Referring now to FIG. 1, a first embodiment of apparatus representatively configured and operable in accordance with the teachings of our invention is indicated generally at 10; and comprises a flow conduit 12 of any suitably inert, highly hydrophobic material in the nature for example of an appropriate fluorinated hydrocarbon.

In addition to being highly hydrophobic, fluorinated hydrocarbon materials of the nature utilized in the formation of flow conduit 12 are well known and understood by those skilled in this art to be selectively "wettable" by a wide range, for example, of fluorinated or perfluorinated hydrocarbon, or silicon liquids of very low surface tension, which are also hydrophobic, to the substantial exclusion of aqueous liquids which are immiscible therewith; and this phenomenon of selective "wettability" of hydrophobic materials by these liquids to the substantial exclusion of immiscible aqueous liquids is discussed in some detail in U.S. Pat. No. 3,479,141 issued Nov. 18, 1969 to William J. Smythe, et al, for "Method and Apparatus For Analysis" and assigned to the assignee hereof, the disclosure of which is hereby incorporated by reference in this specification.

U.S. Pat. No. 3,479,141 also discloses the use of this concept of selective "wettability" of hydrophobic materials to minimize aqueous sample liquid carryover, e.g. the contamination of a succeeding aqueous sample liquid by the residue of a preceding aqueous sample liquid, attendant automated, successive aqueous sample liquid analysis. In accordance with that patent disclosure, this is accomplished by the encapsulation within an immiscible hydrophobic silicone liquid of the successive aqueous sample liquids of a continuously flowing stream thereof as the same progresses through a fluorinated hydrocarbon flow conduit length; with the silicone liquid functioning as an isolation liquid to isolate the aqueous sample liquids, one from the other, to prevent contact and cross-contamination therebetween, and functioning as an isolation liquid to selectively "wet" the inner flow conduit wall to the substantial exclusion of the aqueous sample liquids thereby isolating those sample liquids from that inner flow conduit wall and preventing a preceding aqueous sample liquid from contacting the same and leaving a residue thereon for pick-up by and contamination of a succeeding aqueous sample liquid.

Other United States Patents which relevantly disclose the application of this concept of selective "wettability" of hydrophobic conduit materials by a hydrophobic isolation liquid to the substantial exclusion of aqueous sample liquids which are immiscible therewith for the minimization of aqueous sample liquid carryover attendant automated, successive aqueous sample liquid analysis are U.S. Pat. No. 4,253,466 issued Mar. 3, 1981 to William J. Smythe, et al, for "Method and Apparatus For Automated Analysis Of Fluid Samples," and assigned to the assignee hereof, U.S. Pat. Nos. 4,121,466 and 4,357,301 as referred to hereinabove under the "Description of the prior art," and U.S. Pat. No. 4,517,302 issued May 14, 1986 to Steven Saros, et al, for "Sample Analysis System," and assigned to the assignee hereof; and the disclosures of each of these United States Patents are also incorporated by reference in this specification.

Sampler and sample processor means are indicated schematically at 14 in FIG. 1: and may, for example, take the general form of those disclosed in U.S. Pat. No. 4,121,466 wherein the same are operable to generate an air-segmented stream 16 of isolation liquid-encapsulated successive aqueous sample liquid segments in hydrophobic flow conduit 12, thereby minimizing carryover between those aqueous sample liquid segments, and significantly increasing the accuracy of the sample liquid analysis results. In addition, sampler and sample processor means 14 will readily be understood by those skilled in this art to include any and all sample liquid processing components as required for the particular sample liquid analysis of interest; and these may include but not be limited to components for the addition of appropriate reagent(s) to the sample liquids, and sample liquid dilution, heating, incubation and/or mixing components.

As illustrated in FIG. 1, air-segmented sample liquid stream 16 comprises alternating sample liquid segments S1, S2, S3, S4, S5, and S6, as respectively separated in turn by air segments A1, A2, A3, A4, and A5; all as respectively encapsulated as shown by thin layers of the immiscible isolation liquid as indicated at 20 between the respective sample liquid and air segments. Although the respective thicknesses of the isolation liquid layers 18 and 20 may vary in accordance with the particular sample liquid analysis application in question, it may be understood that, in accordance with the extremely high costs of suitable isolation liquids which may, for example, approach $1,000 per gallon, contemporary versions of the sampler here under discussion have been developed with the capability of generating extremely thin, although nonetheless fully effective isolation liquid encapsulating layers 18 and 20. In fact, it will be clear to those skilled in this art that natural spreading and hydrodynamic forces tend to force excess isolation liquid to the inner wall of conduit 12, thus maintaining extremely thin inter-segment isolation liquid layers 20, especially at the generally central portions thereof, even under relatively "rich" isolation liquid conditions. For example, and with particular regard to the inter-segment isolation liquid layers 20 of FIG. 1 which are not in contact with the highly hydrophobic inner wall of flow conduit 12, generation of such layers of essentially monolayer or single molecule thickness, at least at the generally central portions thereof, is now believed to be possible.

Liquid separator means are indicated generally at 22 in FIG. 1 and comprise a generally L-shaped tubular probe 23 including a probe length 24 which extends as shown through the wall of flow conduit 12, and a connected probe length 26 which extends therefrom within flow conduit 12 concentrically thereof in the upstream direction with regard to air-segmented sample liquid stream 16. Sealing means are indicated at 28 and are disposed at the juncture of probe length 24 and flow conduit 12 to prevent leakage from the flow conduit at that juncture.

Figure 2:
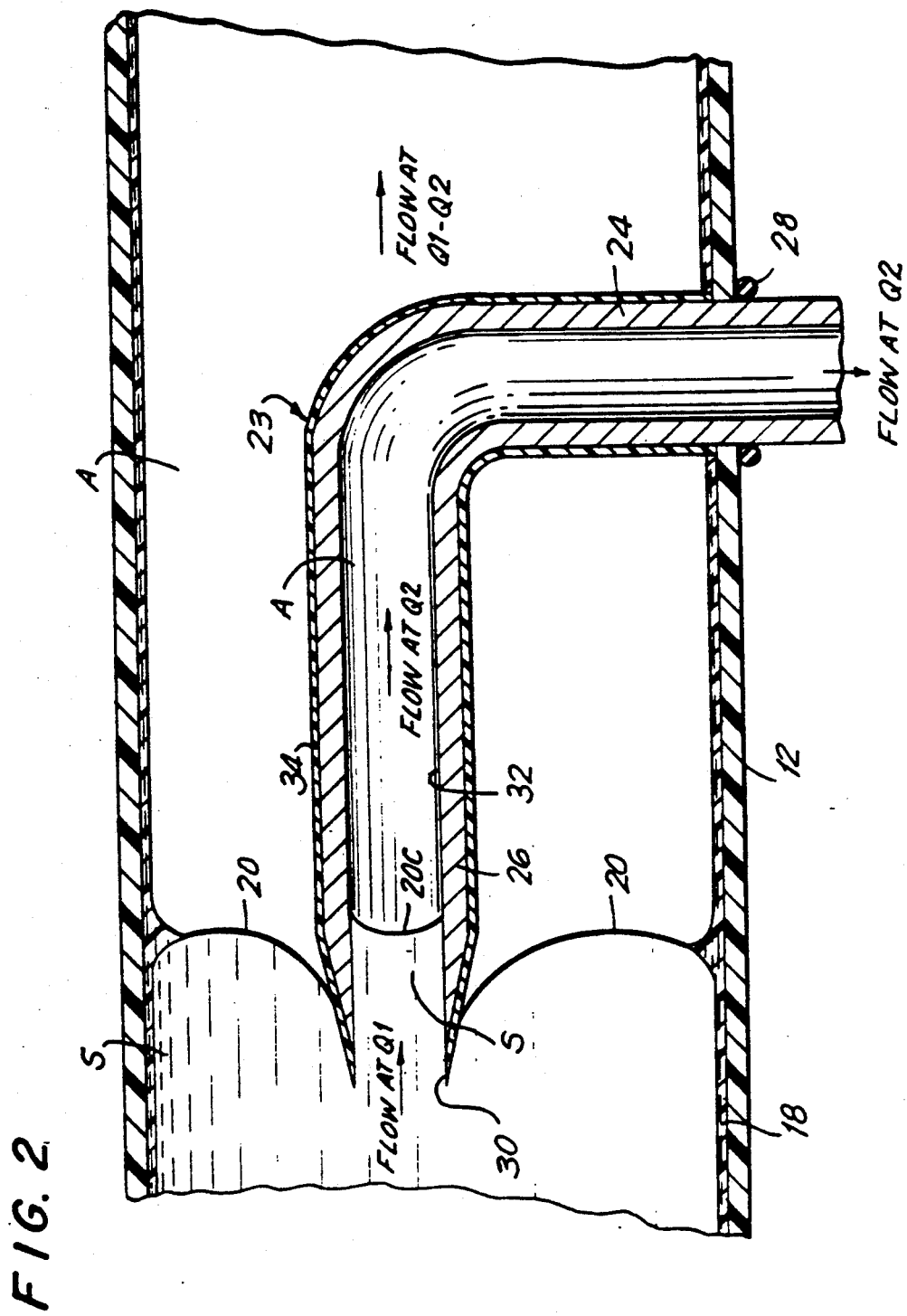
FIG. 2 is an enlarged cross-sectional view of the probe means of the apparatus of FIG. 1.

As best seen in FIG. 2, probe length 26 includes a sharp-edged inlet end 30 communicating the internal probe flow passage 32 with the air segmented sample liquid stream 16 in flow conduit 12.

Probe 23 is fabricated from any appropriately inert, hydrophilic material, for example stainless steel as shown, or glass; and, as best seen in FIG. 2, the exterior of probe 23 which is exposed to the air segmented sample liquid stream 16 within flow conduit 12 is surface coated with an appropriately inert, highly hydrophobic material in the nature, for example of a fluorinated hydrocarbon, as indicated at 34. Under these circumstances, it will be clear to those skilled in this art that the isolation liquid will be preferentially attracted to the highly hydrophobic surface coating 34 at the exterior of probe 23 to "wet" the same to the substantial exclusion of the aqueous sample liquids, while the aqueous sample liquids will in turn be preferentially attracted to the hydrophilic wall of the internal probe flow passage 32 to "wet" the same; and the resultant essentially natural capability of the probe 23 to effectively discriminate between the aqueous sample liquids and the immiscible isolation liquid, especially at the sharp-edged probe inlet 30, will be seen to be of particular significant advantage with regard to the effective separation of those liquids as described in detail hereinbelow.

Although dimensions may of course vary in accordance with the particular application(s) to which the apparatus of our invention is put, it may be understood that with a flow conduit 12 of nominally 1.50 mm inner diameter, a representative outer diameter for probe lengths 24 and 26 would be nominally 0.75 mm, with a nominal diameter for internal probe passage 32 of 0.25 mm, to thus provide a probe length wall thickness of nominally 0.25 mm. Under these conditions, a representative nominal length for probe length 26 would be 1.50 cm.

For reasons made clearer hereinbelow, it is of particular importance that the probe length 26 be centered as precisely as possible vis-a-vis flow conduit 12 to insure that the probe intercepts the most central, and thus lowest isolation liquid volume-bearing, portion of sample liquid stream 16; and that the probe length 26 be of the smallest practical wall thickness to insure minimal adverse effect thereof on the hydrodynamics of the sample liquid stream 16 at the juncture thereof.

Additional sample liquid processing and/or sample liquid analysis means are indicated schematically at 36 in FIG. 1 and may take any appropriate form(s) compatible with automated successive sample liquid processing and/or analysis. Most relevantly with regard to the apparatus of our invention, and for applications thereof to the automated successive processing and quantitative analysis in turn of a series of blood samples, the additional sample liquid processing means may, for example, comprise a dialysis device; while the sample liquid analysis means may, for example, comprise colorimetric, spectroscopic, ion selective electrode, cell counting, enzyme coil and/or dry chemistry slide analytical devices, wherein the continued presence of the isolation liquid with the sample liquids can interfere with the requisite highly precise operation of those analysis devices with resultant, and contemporarily unacceptable, degradation in the accuracy of the sample analysis results. For application of the apparatus of our invention wherein no additional processing of the aqueous sample liquids from flow conduit 12 is required prior to the automated successive analysis thereof, means 36 would of course be limited to sample analysis device(s).

A secondary flow conduit is shown at 38 in FIG. 1, and is connected as indicated through pump 39 to the additional sample liquid processing and/or sample liquid analysis means 36 to supply sample liquids thereto in turn at a flow rate Q2 in accordance with the output of pump 39. Although representatively depicted as of essentially the same dimension as flow conduit 12, it will be clear to those skilled in this art that secondary flow conduit 38 may be of any dimension and composition compatible with additional sample liquid processing and/or analysis, for example standard laboratory tubing. With secondary flow conduit 38 of essentially the same dimension as flow conduit 12, and thus of significantly greater outer diameter than probe length 24, an essentially L-shaped connecting piece 40, including an enlarged end portion 42, of essentially the same size as secondary flow conduit 38, is provided to connect the outlet end of probe length 24 to the inlet end of secondary flow conduit 38 as shown, and of course in fluid-tight manner. Alternatively, connecting piece 40 may, for example, be formed integrally with probe 23.

Isolation liquid recovery means are indicated schematically at 44 in FIG. 1 and may take any form compatible with the effective recovery of the isolation liquid, which may be quite expensive as set forth hereinabove, from the sample liquids, for re-use of the isolation liquid. Since, in the vast majority of instances, the isolation liquid will be of different specific gravity than the sample liquids, the recovery of the isolation liquid may be effectively accomplished in unhurried manner by simply allowing the respective sample and isolation liquids to settle out at different levels under the force of gravity in the same container, and subsequently removing the isolation liquid therefrom for re-use.

Flow conduit 12 is connected as indicated in FIG. 1 to isolation liquid recovery means 44 to supply the isolation liquid-rich sample liquid stream 16 thereto.

A system controller is indicated schematically at 48 in FIG. 1, and may for example take the form of an appropriately programmable microprocessor device. Controller 48 is electrically connected as indicated by lines 50, 52 and 54 to sampler and sample processing means 14, pump 39, and additional sample processing and/or sample analysis means 36 to control and synchronize the respective operations thereof.

In operation of the apparatus 10 for the removal of substantially isolation liquid free sample liquid and air segment portions from flowing air segmented sample liquid stream 16 in flow conduit 12, and the supply of the same in turn in the form of a substantially isolation liquid free, air segmented sample liquid stream as indicated at 58 in FIG. 1 in secondary flow conduit 38 to additional sample liquid processing and/or analysis means 36 for successive analysis in turn of each of those sample liquid segment portions, it may be understood that pump 39 is preferably operated by controller 48 at a flow rate $Q2$ which is slightly less than the flow rate $Q1$ at which the air segmented sample liquid stream 16 is flowed in flow conduit 12 immediately upstream of the inlet edge 30 of the probe means 23. A representative example of the ratio $Q2/Q1$ is 0.90, whereby will be clear that nearly all of the sample liquid stream 16 will be withdrawn from flow conduit 12 by probe means 23 for flow as sample liquid stream 58 in secondary flow conduit 38. Under these conditions, the flow rate of the remainder of sample liquid stream 16 in flow conduit 12 downstream of probe means 23 to the isolation liquid recovery means 44 will as indicated be equal to $Q1-Q2$. Of course, it will be immediately clear to those skilled in this art that pumping arrangements other than that shown, for example, differential pumping or pressure pumping, may be utilized to achieve the desired ratio between $Q2$ and $Q1$.

FIG. 2 makes clear that as each inter-segment isolation liquid layer 20 in air segmented sample liquid stream 16 is flowed into contact with the sharp inlet edge 30 of probe means 23, that isolation liquid layer will be cleanly cut by the same, with only the particularly low isolation liquid volume of the most central portion of that isolation liquid layer as indicated at 20C in FIG. 2 being withdrawn along with the sample liquid from the sample liquid segment of interest as shown into the internal probe means flow passage 32 for flow as described into and through secondary flow conduit 38.

Of particular significance in accordance with the teachings of our invention are the facts that the remainder of the isolation liquid layer 20 of interest, e.g. that portion thereof disposed radially outward of probe means inlet edge 30 and which will most probably reform in each instance as shown in FIG. 1 into a very thin isolation liquid layer 20D, and all of the vastly greater isolation liquid volume bearing layer 18 which resides primarily at the inner wall of flow conduit 12, and which will thus be greatly "enriched" vis-a-vis the reduced volume sample liquid segment of interest in each instance as shown at 18D in FIG. 1, will respectively remain in sample liquid stream 16 downstream of the probe means inlet edge 30 for flow as described therewith to the isolation liquid recovery means 44; and it will be immediately clear to those skilled in this art that the highly hydrophobic surface coating 34 on the external surface of probe means 23, and the highly hydrophobic inner wall surface of flow conduit 12—both of which operate as described to strongly attract the isolation liquid to the substantial exclusion of the aqueous sample liquids—will also operate to particularly significant advantage in this regard. Of course, the hydrophilic surface of the internal probe means flow passage 32 which selectively attracts the aqueous sample liquids is also of significant advantage in this regard.

In accordance with the above, the apparatus 10 of our invention will be understood to operate to provide a substantially isolation liquid free air-segmented sample liquid stream 58 in secondary flow conduit 38 for flow as described to additional sample liquid processing and/or analysis means 36 for highly accurate, automated successive sample liquid analysis; it having been determined by actual tests that the extremely small amounts of isolation liquid 20C which do remain in sample liquid stream 58, and which will most probably simply disperse throughout the respective sample liquid segments thereof as shown in FIG. 1, will, in the vast majority of instances, be of no clinical significance with regard to adverse effect upon the overall efficiency and/or accuracy of the operation of the additional sample liquid processing and/or sample liquid analysis means 36.

Figure 3:
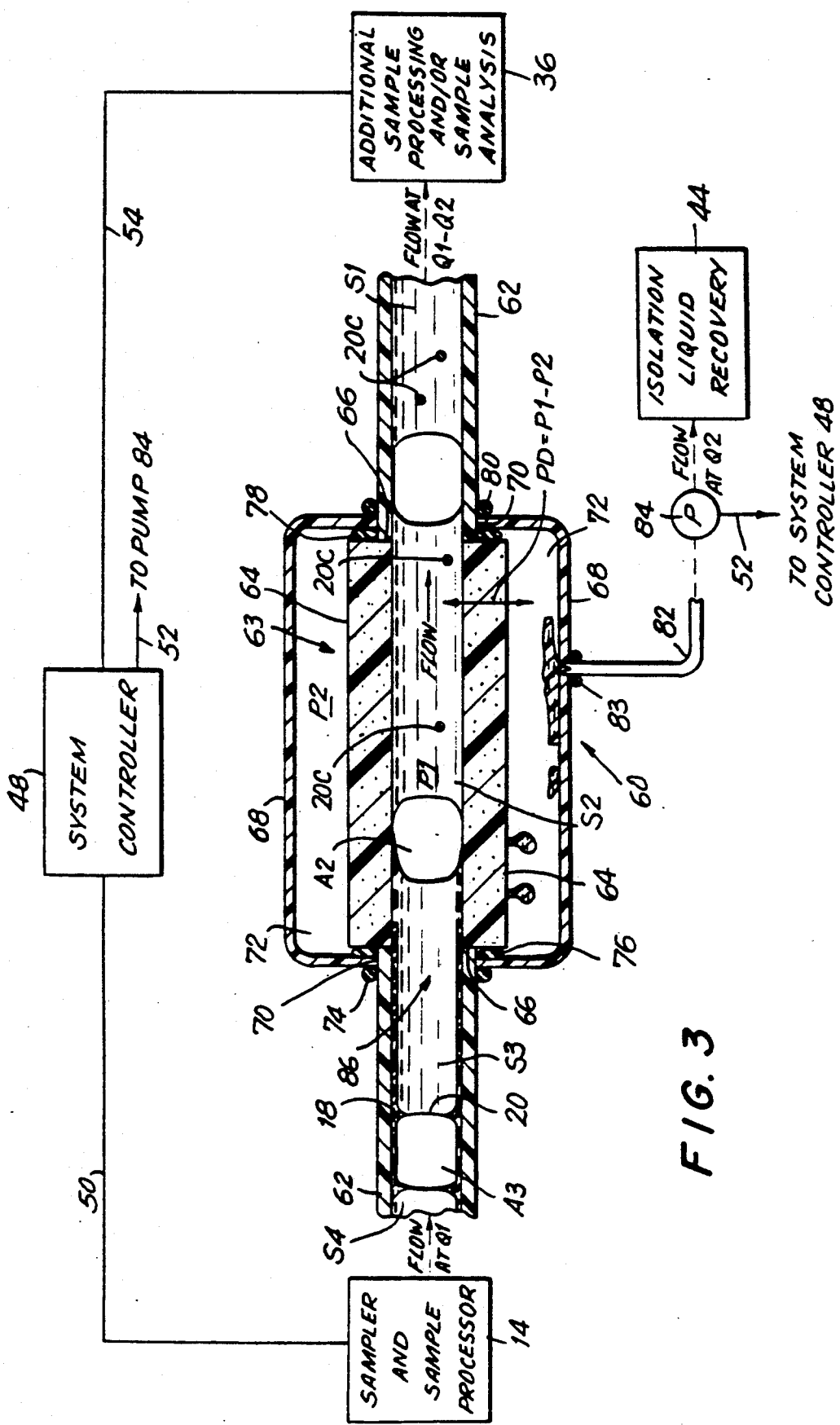
FIG. 3 is an essentially schematic diagram, with certain parts in cross-section, of a sample liquid analysis system including apparatus representatively configured and operable in accordance with the teachings of a second embodiment of our invention for substantially separating one or more liquids out of a flowing stream of immiscible liquids on a continuous flow basis.

A second embodiment of apparatus representatively configured and operable in accordance with the teachings of our invention is indicated generally at 60 in FIG. 3; and comprises a flow conduit 62, again of any suitably inert, highly hydrophobic material in the nature of an appropriate fluorinated hydrocarbon.

Liquid separator means are indicated generally at 63 in FIG. 3 and comprise a conduit insert 64 which is preferably of the same inner diameter as flow conduit 62, and which is joined therein and attached thereto as shown in fluid-tight manner by, for example, a suitable adhesive as indicated at 66 in FIG. 3. Insert 64 is fabricated from any suitably porous filter material which is also highly hydrophobic, again for example an appropriate fluorinated hydrocarbon.

A generally coaxial sleeve is indicated at 68 and is secured as shown in fluid-tight manner to the adjacent external walls of flow conduit 62, again for example by a suitable adhesive as indicated at 70, to surround conduit insert 64 and provide a generally torous-like enclosed space 72 therebetween. Sleeve 68 is made of any suitable, fluid-tight material, for example a suitable plastic. Annular seals 74, 76, 78 and 80 are respectively provided as shown at the junctures of the insert 64 and the sleeve 68 with the flow conduit 62 to prevent fluid leakage therefrom. Alternatively, these junctures may be formed by fluid-tight press fits.

A secondary flow conduit is indicated at 82 in FIG. 3 and extends as shown through porous insert 64 at the lower portion thereof into communication with enclosed space 72. A fluid-tight annular seal 83, or a like press fit, is utilized to prevent fluid leakage at this juncture. Secondary flow conduit 82 is connected as indicated through pump 84 to supply isolation liquid from space 72 to isolation liquid recovery means as again indicated schematically at 44, and which may take the same form as described hereinabove with regard to the embodiment of FIG. 1.

Sampler and sample processor means, additional sample processing, and/or sample analysis means, and system controller are respectively again indicated schematically at 14, 36 and 48; and, in each instance, may take the same form as described hereinabove with regard to the embodiment of FIG. 1.

In the operation of apparatus 60 of FIG. 3, sampler and sample processor means 14 are again operable as described to generate an air-segmented stream as there indicated at 86 of isolation liquid encapsulated successive aqueous sample liquid segments in flow conduit 62; and this stream 86 will be seen in FIG. 3 to comprise alternating aqueous sample liquid segments S1, S2, S3, and S4, as respectively separated in turn by air segments A1, A2, and A3; all as respectively encapsulated as shown by thin layers of the isolation liquid as again indicated at 18 between the respective sample liquid and air segments and the inner wall of flow conduit 62, and as again indicated at 20 between the respective sample liquid and air segments.

With air-segmented sample liquid stream 86 flowing as described in flow conduit 63 at a pressure P1, and with pump 84 operated by controller 48 to create a lower pressure P2 in sleeve space 72 through secondary flow conduit 82, a differential pressure PD is created across the porous hydrophobic conduit insert 64. As a result, as each of the respective aqueous sample liquid segments S and air segments A flows into insert 64, this differential pressure PD taken in conjunction with the interfacial tension driving forces arising from the selective attraction of the isolation liquid to the highly hydrophobic material of the insert 64, will operate to draw the isolation liquid layers 18 at the insert wall essentially in their respective entireties and, to a somewhat lesser extent, the inter-segment isolation liquid layers 20, through the porous hydrophobic insert 64 into the sleeve space 72 as shown in FIG. 3 thereby separating the same from the segmented sample liquid stream 86. With more specific regard to the inter-segment isolation liquid layers 20, it will be clear that the same will, in effect, be naturally drawn to the inner wall of porous insert 64 upon the removal of the isolation liquid layer 18 for removal from the sample liquid stream 86 therethrough as a result of spreading and hydrodynamic forces; with the remaining very small portions of those inter-segment layers 20 which are not so drawn most probably simply dispersing throughout the sample liquid segment as indicated at 20C in FIG. 3 in and downstream of the insert 64. The high interfacial tension between the aqueous sample liquid segments and the porous hydrophobic insert 64 will operate to substantially inhibit aqueous sample liquid passage through insert 64.

Under the above circumstances, it will be clear to those skilled in this art that proper selection of the differential pressure PD and the pore size of the porous insert 64, it becomes possible to withdraw substantially only isolation liquid, plus some measure of air from the respective air segments A which is of no clinical significance, from the air-segmented sample liquid stream 86 into sleeve space 72 as described; while appropriate selection of the length of the insert 64 in accordance with the above can be utilized to insure that the maximum quantity of the isolation liquid which can, as a practical matter, be withdrawn from the stream 86 will, in fact, be withdrawn therefrom attendant the transit by the stream of the insert 64. Although these controlling parameters may, of course, vary in accordance with the particular application(s) to which the apparatus of our invention is put, values thereof for a representative application of that apparatus with an insert of nominally 1.50 mm inner diameter and a nominal length of 3.0 cm, would be a nominal pore size of 2.0 microns for the porous insert 64, and a nominal pressure differential PD equal to P1–P2 across the insert 64 of up to 10 psi to provide for the withdrawal of substantially only the isolation liquid and some measure of air as described through the porous insert 64 into sleeve space 72.

For application of the apparatus 60 wherein the maximum achievable removal of the isolation liquid from the air-segmented sample liquid stream 86 is required, and wherein some relatively small loss of the aqueous sample liquids through porous insert 64, for example 5.0% by volume, can be accommodated without adverse effect upon the accuracy of the sample liquid analysis results, it will be clear that the pore size of the porous insert 64, the differential pressure PD, and/or the length of porous insert 64 can be increased to that effect.

FIG. 3 makes clear that the isolation liquid which is withdrawn as described through porous insert 64 into space 72, plus any air and/or aqueous sample liquids as may be included therewith, will be pumped by pump 84 to isolation liquid recovery means 44 for isolation liquid recovery and re-use, if desired, as described herein above with regard to the embodiment of FIG. 1. Concomitantly, the now substantially isolation liquid-free air-segmented sample liquid stream 86, including substantially only the remaining very low isolation liquid volume-bearing isolation liquid layer portions 20C, will exit sleeve 64 for flow as indicated through conduit to additional sample processing and/or sample analysis means 36 for highly accurate, automated successive aqueous sample liquid processing and/or analysis; it having also been determined by the actual test of the apparatus 60 of our invention that the extremely small amounts of isolation liquid 20C which do remain as described in the sample liquid stream 86 will, in the vast majority of instances, be of no clinical significance with regard to adverse effect upon the operation of the additional sample liquid processing and/or analysis means 36.

Figure 4:
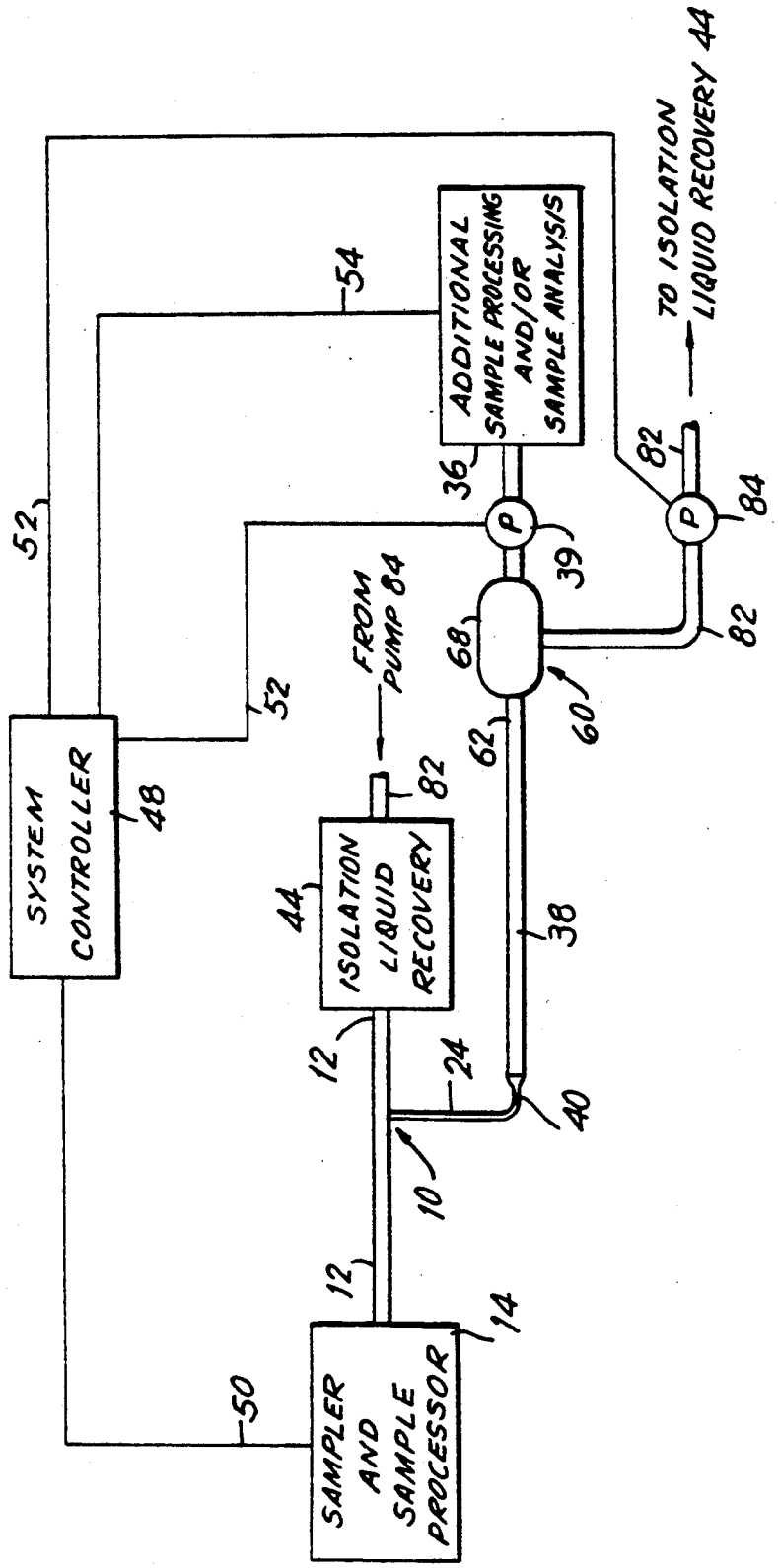
FIG. 4 is an essentially schematic diagram, of a continuous flow sample liquid analysis system including the embodiment of the liquid separating apparatus of our invention of both FIG. 1 and FIG. 3.

For certain applications of the apparatus and method of our invention wherein an absolute maximum of achievable isolation liquid stream is required prior to additional sample liquid processing and/or analysis, the liquid separator means of our invention may be serially connected or cascaded. FIG. 4 schematically depicts a representative apparatus arrangement to that effect wherein the liquid separator means 22 of FIG. 1 and the liquid separator means 63 are serially connected in that order. In operation, it will be clear that the substantially isolation liquid-free air-segmented sample liquid stream 58 from secondary flow conduit 38 of FIG. 1 would be flowed in turn as air-segmented sample liquid stream 86 through flow conduit 62 of FIG. 3 by pump 39 for additional isolation liquid removal therefrom as described within sleeve 68 of FIG. 3; it being noted in this regard that the very small isolation liquid quantities initially remaining in stream 58 as formed by the central portions 20C of isolation liquid layers 20 will most probably soon migrate within secondary flow conduit 38 to the inner wall thereof—which, in this instance, would of course be made from a highly hydrophobic material—to again provide for significant inhibition of sample liquid carryover therein, and to enable the subsequent, highly effective removal thereof from the flowing sample liquid stream 86 in flow conduit 62 by the withdrawal thereof as described through porous conduit insert 64 within sleeve 68 as described. In this instance, flow conduit 12 and secondary flow conduit 82 would be connected as indicated to the same isolation liquid recovery means 44.

As alternatives to the serial liquid separator means arrangement of FIG. 4, it will be clear to those skilled in this art that the same could be serially connected with the liquid separator means 63 of FIG. 3 ahead of the liquid separator means 22 of FIG. 1, and that two or more of the same liquid separator means 22 or 63 could be serially connected as such; again in any event to improve the overall efficiency of the isolation liquid removal process.

Although disclosed in detail hereinabove as applied to the particularly effective substantial separation of the isolation liquid from an isolation liquid encapsulated, segmented sample liquid stream prior to sample liquid analysis to improve the accuracy thereof, it will be clear that the embodiments of the liquid separating apparatus 10 and 60 of our invention can alternatively be applied to that purpose solely for isolation liquid reclamation following sample analysis in those instances wherein the sample liquid analysis can be satisfactorily performed with the isolation liquid layers essentially in place as described. In such applications, the substantially isolation liquid-free sample liquid streams downstream of the separating apparatus would most probably simply be flowed to waste.

Figure 5:
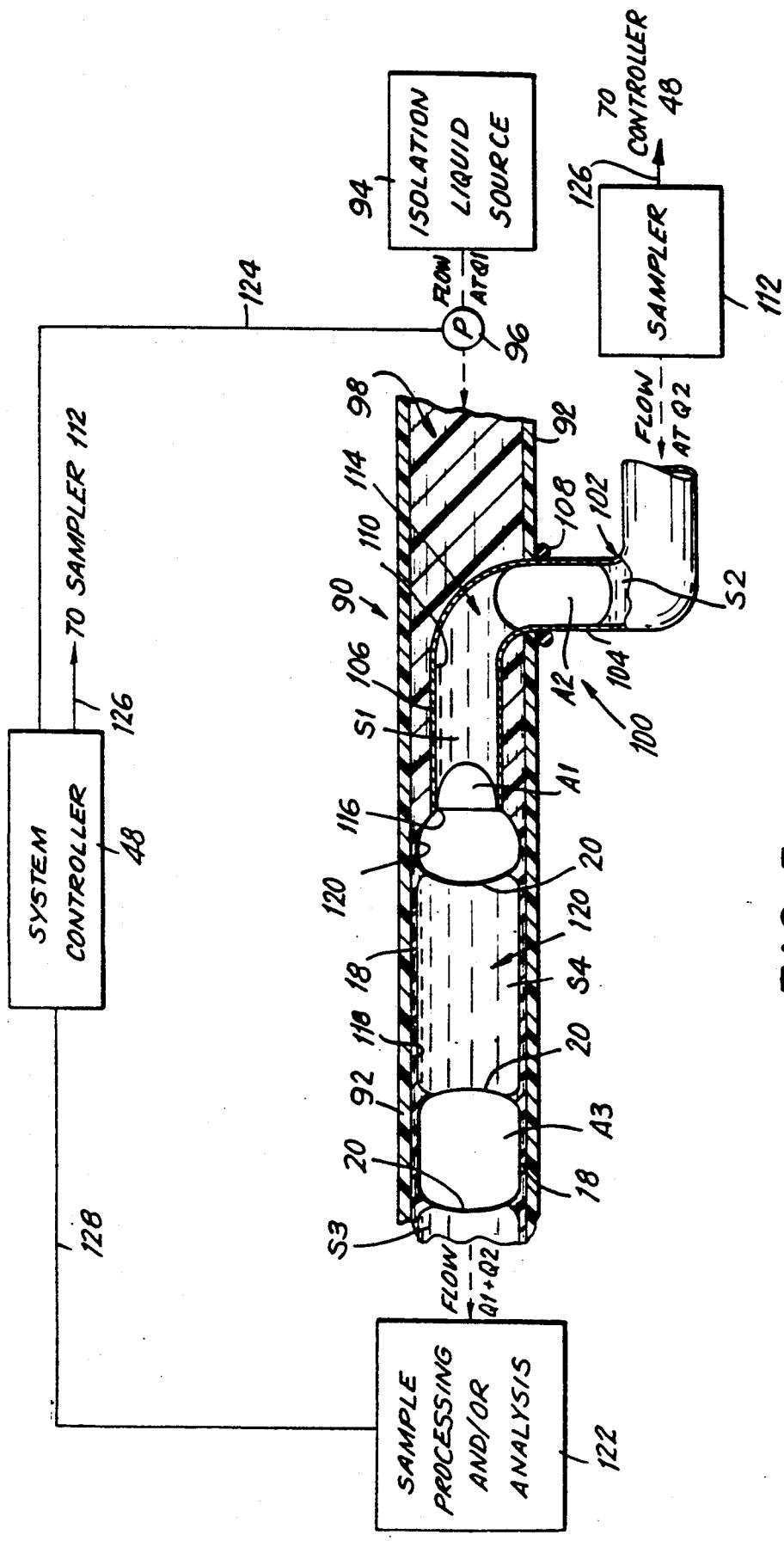
FIG. 5 is an essentially schematic diagram, with certain parts in cross-section, of a sample liquid analysis system including apparatus representatively configured and operable in accordance with the teachings of a third embodiment of our invention for introducing one or more liquids into a flowing stream of liquid which is immiscible therewith to form a flowing stream of said immiscible liquids on a continuous flow basis and wherein one said liquids substantially encapsulates another of said liquids.

A third embodiment of apparatus representatively configured and operable in accordance with the teachings of our invention is indicated generally at 90 in FIG. 5; and comprises a flow conduit 92, again of any suitably inert, highly hydrophobic material in the nature of an appropriate fluorinated hydrocarbon.

An isolation liquid source is indicated schematically at 94, and is connected as shown through pump 96 to supply a stream 98 of the isolation liquid for flow through the conduit 92 in the direction indicated.

Liquid introduction means are indicated generally at 100 in FIG. 5, and comprise a generally L-shaped tubular probe 102 including a probe length 104 which extends as shown through the wall of flow conduit 92, and a connected probe length 106 which extends therefrom within flow conduit 92 concentrically thereof in the upstream direction with regard to isolation liquid stream 98. Sealing means are indicated at 108 and are disposed at the juncture of probe length 104 and conduit 92 to prevent fluid leakage at that juncture. Probe 102 includes an internal flow passage 110 extending therethrough as shown; and is fabricated from any appropriately inert material, for example stainless steel as shown, or glass.

Although dimensions may, of course, vary in accordance with the particular application(s) to which the apparatus of our invention is put, it may be understood that with a flow conduit 92 of nominally 1.50 mm inner diameter, a representative outer diameter for probe lengths 104 and 106 would be nominally 1.3 mm, with a nominal diameter for internal probe flow passage 110 of 1.0 mm, to thus provide probe wall thicknesses of nominally 0.15 mm. Under these conditions, a representative nominal length for probe length 106 would be 1.50 cm. For reasons made clearer hereinbelow, it is again of particular importance that probe length 106 be centered as precisely as possible vis-a-vis flow conduit 92 to insure that this probe length lies in the most central portion of the isolation liquid stream 98 flowing therearound. Minimal probe wall thickness is also again of importance.

Sampler means are indicated schematically at 112 in FIG. 5 and are operable in conventional manner to supply an air-segmented stream 114 of sample liquid segments as shown to probe 102 for flow therethrough through internal probe flow passage 110 to merge with the isolation liquid stream 98 as the stream 114 exits the outlet edge 116 of the probe length 106. As illustrated in FIG. 5, stream 114 comprises sample liquid segments S1 and S2 and air segments A1 and A2.

In operation, FIG. 5 makes clear that as each air segment, for example air segment A1 as shown, exits the internal probe flow passage 110 through outlet edge 116 of the probe length 106, that air segment will naturally expand in diameter to essentially fill the larger diameter internal flow passage 118 of the conduit 92 and, in so doing, the segment or bubble meniscus 120 will pick up the flowing isolation liquid from isolation liquid stream 98 and displace and distribute the same in the form of the isolation liquid layer 18 at the wall 118 of that internal conduit flow passage to coaxially surround the air segment of interest.

The immediately following flow of the succeeding sample liquid segment S1 from the internal probe flow passage 110 into the isolation liquid stream 98 in internal flow conduit passage will, as that sample liquid segment naturally expands in diameter in like manner to essentially fill the larger diameter flow passage 118 of the conduit 92, continue this displacement and distribution of the isolation liquid, thereby continuing the formation of the isolation liquid layer 18. Of course, the preferential "wettability" of the highly hydrophobic wall of the internal conduit flow passage 118 by the isolation liquid to the substantial exclusion of the aqueous sample liquids virtually insures against any contact by the aqueous sample liquids with that internal conduit flow passage wall attendant the flow of the sample liquid stream 114 into conduit 92 as described. This, in turn, virtually insures the formation and retention in conduit 92 downstream of probe 102 of a continuous, air and sample liquid stream encapsulating isolation liquid layer 18. In addition, and as each air segment, for example A1, exits the probe 102 for expansion as shown in FIG. 5 within the isolation liquid stream 98 in conduit 92, the same will also operate to displace the isolation liquid from that stream to continue the formation of the isolation liquid layer 18, and to form the inter-sample liquid segment isolation liquid layers 20 as shown in FIG. 5 at the respective air-sample liquid segment interfaces.

In accordance with the above, the resultant isolation liquid-encapsulated, air-segmented sample liquid stream 120 in conduit 92 in FIG. 5 downstream of probe length 106 and, which as illustrated comprises sample liquid segments S3 and S4, and air segment A3, will be fully protected against sample liquid carryover by the isolation liquid layer.

Sample liquid processing and/or analysis means are indicated schematically at 122 in FIG. 5, and are operable as indicated to receive the isolation liquid encapsulated, air-segmented sample liquid stream 120 from conduit 92 to those purposes. In this instance, sample liquid processing and/or analysis means 122 would take the form of those which are satisfactorily operable to those purposes without degradation of clinical significance in sample liquid processing and/or analysis with the isolation liquid layer 18 in place.

A system controller is again indicated schematically at 48 in FIG. 5, and is operable as indicated through lines 124, 126 and 125 to synchronize and control the operation of pump 96, sampler 112, and sample processing and/or analysis means 122.

With pump 96 supplying the isolation liquid stream 198 to flow conduit 92 at a flow rate Q1, and sampler 112 supplying the air-segmented sample liquid stream 114 to flow conduit 92 at a flow rate Q2, it will be clear that the flow rate Q3 of stream 120 in flow conduit 92 will be equal to Q1 and Q2. Although these flow rates, and the ratio between flow rate Q2 and Q1 may, of course, vary throughout wide ranges in accordance with the application(s) to which the apparatus of 90 of FIG. 5 are put, it may be understood that a representative range for the ratio Q2/Q1 is between 10 to 1 and 100 to 1 in accordance with the required "richness" of the isolation liquid layer 18 relative to stream 120.

Of particular advantage with regard to the apparatus 90 of FIG. 5 are the facts that the same operates to precisely form the isolation liquid layer 18 where it is most needed and most effective for purposes of minimization of sample liquid carryover, e.g. at the inner wall 118 of flow conduit 92, and that precise and readily accomplishable control in each instance of the flow rate ratio Q2/Q1 enables the precise formation of the isolation liquid layer of the optimal thickness in accordance with the particular application to which the apparatus 90 are to be put with regard to both sample liquid carryover minimization and economy of isolation liquid utilization.

Figure 6:
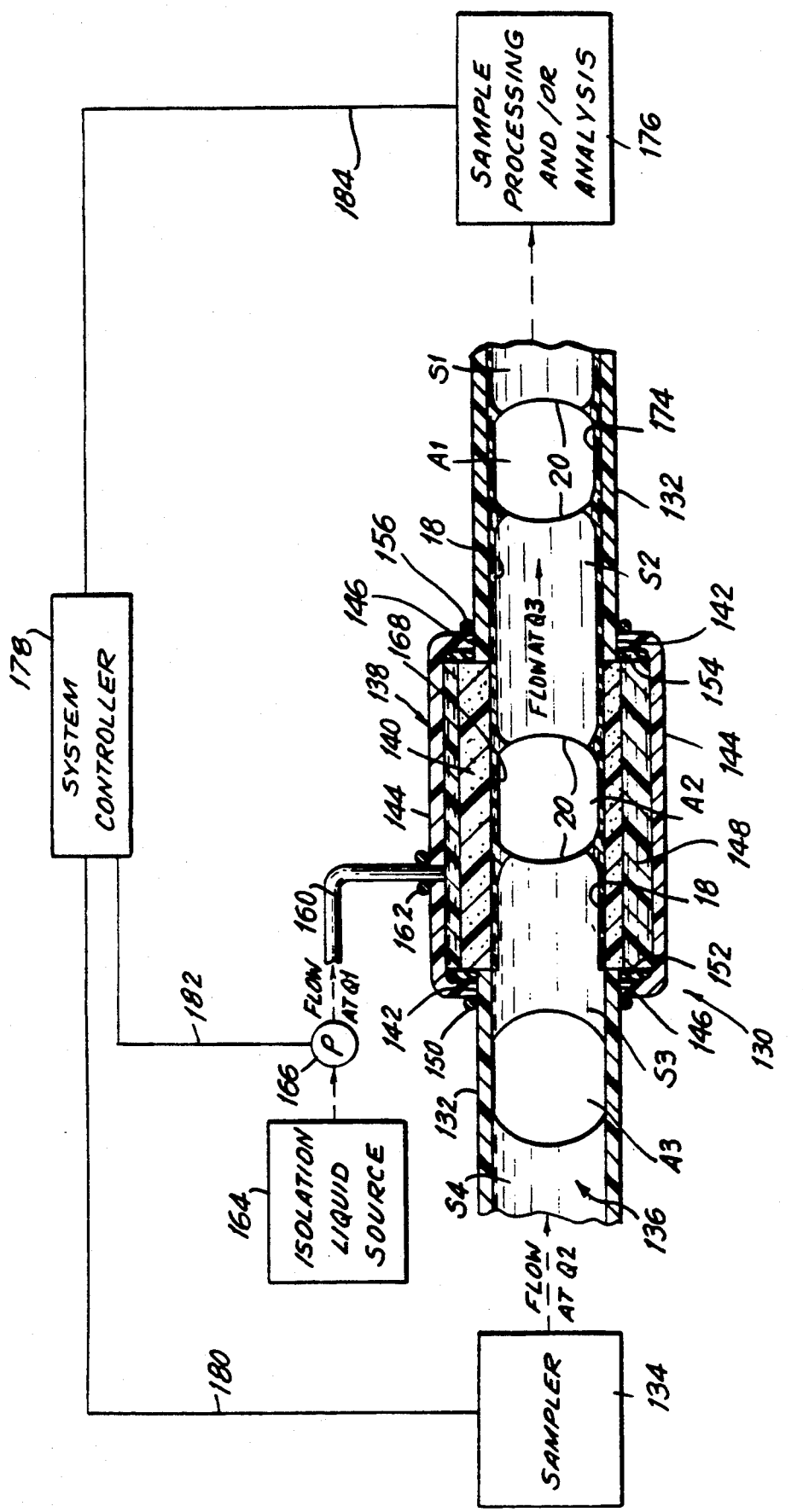
FIG. 6 is an essentially schematic diagram, with certain parts in cross-section, of a sample liquid analysis system including apparatus representatively configured and operable in accordance with the teachings of a fourth embodiment of our invention for introducing a liquid into a flowing stream of one or more liquids which are immiscible therewith to form a flowing stream of said immiscible liquids on a continuous flow basis and wherein one of said liquids substantially encapsulates another of said liquids.

A fourth embodiment of apparatus representatively configured and operable in accordance with the teachings of our invention is indicated generally at 130 in FIG. 6; and comprises a flow conduit 132, again of any suitably inert, highly hydrophobic material in the nature of an appropriate fluorinated hydrocarbon.

A sampler is indicated schematically at 134 and is operable as indicated in conventional manner to supply an air-segmented sample liquid stream 136 for flow through the internal flow passage 138 of conduit 132. As illustrated in FIG. 6, stream 136 comprises sample liquid segments S1, S2, S3 and S4 as separated by air segments A1, A2 and A3.

Liquid introduction means are indicated generally at 138 in FIG. 6, and take much the same form structurally as the liquid separator means 63 of FIG. 3. To that effect, liquid introduction means 138 comprise a conduit insert 140 which is preferably of the same inner diameter as flow conduit 132, and which is joined therein and attached thereto as shown in fluid-tight manner by, for example, a suitable adhesive as indicated at 142 in FIG. 6. Insert 140 is fabricated from any suitably porous filter material which is also highly hydrophobic, again for example an appropriate fluorinated hydrocarbon.

A generally coaxial sleeve is indicated at 144 and is secured as shown in fluid-tight manner to the adjacent external walls of conduit 132, again for example by a suitable adhesive as indicated at 146, to surround the conduit insert 144 and provide a generally torous-like enclosed space 148 therebetween. Sleeve 144 is made of any suitable, fluid-tight material, for example a suitable plastic. Annular seals 150, 152, 154 and 156 are provided as shown at the respective junctures of the insert 140 and sleeve 144 with the flow conduit 132 to prevent fluid leakage therefrom. Again, fluid-tight press fits may alternatively be utilized to form these junctures.

An isolation liquid supply conduit is indicated at 160 in FIG. 6 and extends as shown through sleeve 144 into communication with torous-like space 148. An annular seal 162 is disposed around the juncture of conduit 160 and sleeve 144 to prevent fluid leakage therefrom.

An isolation liquid source is indicated schematically at 164 in FIG. 6 and is connected as shown through a pump as schematically indicated at 166 for the supply of isolation liquid through supply conduit 160 to the space 148. Pump 166 is preferably of the positive displacement type taking, for example, the form of a standard laboratory syringe pump which is operable to positively pump liquids at precisely determinable flow rates.

In operation of the apparatus 138 of FIG. 6 to introduce an isolation liquid from source 164 to air-segmented sample liquid stream 136 within insert 140 to encapsulate the latter therewithin, it will be clear that, with torous-like space 148 filled with the isolation liquid, the continued operation of positive displacement pump 166 will function to flow the isolation liquid from space 148 through the porous insert 140 to emerge at the inner wall 168 of the same at the outer boundary of the flowing air segmented sample liquid stream 136 therein. Of course, as the positively pumped isolation liquid emerges from the inner wall 168 of the insert 140, it will displace the air-segmented sample liquid stream 136 therefrom; with the preferential attraction of the isolation liquid to that highly hydrophobic inner wall to the substantial exclusion of the aqueous sample liquids, functioning to retain the isolation liquid in contact therewith to form the isolation liquid layer 18 within insert 140 for flow with the stream 136 through flow conduit 132 in the direction indicated in FIG. 6. In addition, and with a sufficiently "high" ratio of isolation liquid flow Q1 through porous conduit insert 140 to air-segmented sample liquid stream flow Q2 through conduit 132, formation of the respective isolation liquid layers 20 at the respective air and sample liquid segment interfaces as shown in FIG. 6 will also again be accomplished. As a result, it will be clear that sample liquid carryover is again effectively minimized with regard to the isolation liquid-encapsulated, air-segmented sample liquid stream 174 attendant the continued flow thereof in flow conduit 132 downstream of the porous conduit insert 140.

Sample processing and/or analysis means are schematically indicated at 176 in FIG. 6, and operate as indicated to receive the isolation liquid encapsulated, air-segmented sample liquid stream 172 from flow conduit 132 to those purposes; it being clear that, in this instance, sample liquid processing and/or analysis means 176 would take the form of those which are satisfactorily operable without degradation of clinical significance in sample liquid processing and/or analysis with the isolation liquid layers 18 and 20 in place.

A system controller is indicated schematically at 178 in FIG. 6 and is operatively connected as indicated to sampler 134, pump 166, and sample processing and/or analysis means 176 to control and synchronize the respective operations thereof.

With pump 166 supplying the isolation liquid stream through porous insert 140 to flow conduit 132 at a flow rate Q1, and sampler 134 supplying the air-segmented sample liquid stream 136 to that flow conduit at a flow rate Q2, it will be clear that the flow rate Q3 of stream 172 will be equal to Q1 and Q2. Again, these flow rates, and the ratio between Q1 and Q2 may, of course, vary widely as set forth hereinabove with regard to the embodiment of FIG. 5.

Again of particular advantage with regard to the apparatus 130 of FIG. 6 are the facts that the same operates to precisely form the isolation liquid layer 18 where it is most needed and most effective for purposes of minimization of sample liquid carryover, e.g. at the inner wall 168 of the insert 140 and thus at the inner wall 174 of the flow conduit 132, and that precise and readily accomplishable control in each instance of the flow rate ratio Q2/Q1 enables the precise formation of the isolation liquid layer 18 of the optimal thickness in accordance with the particular application to which the apparatus 130 are to be put with regard to both sample liquid carryover minimization and minimization of isolation liquid consumption.

Figure 7:
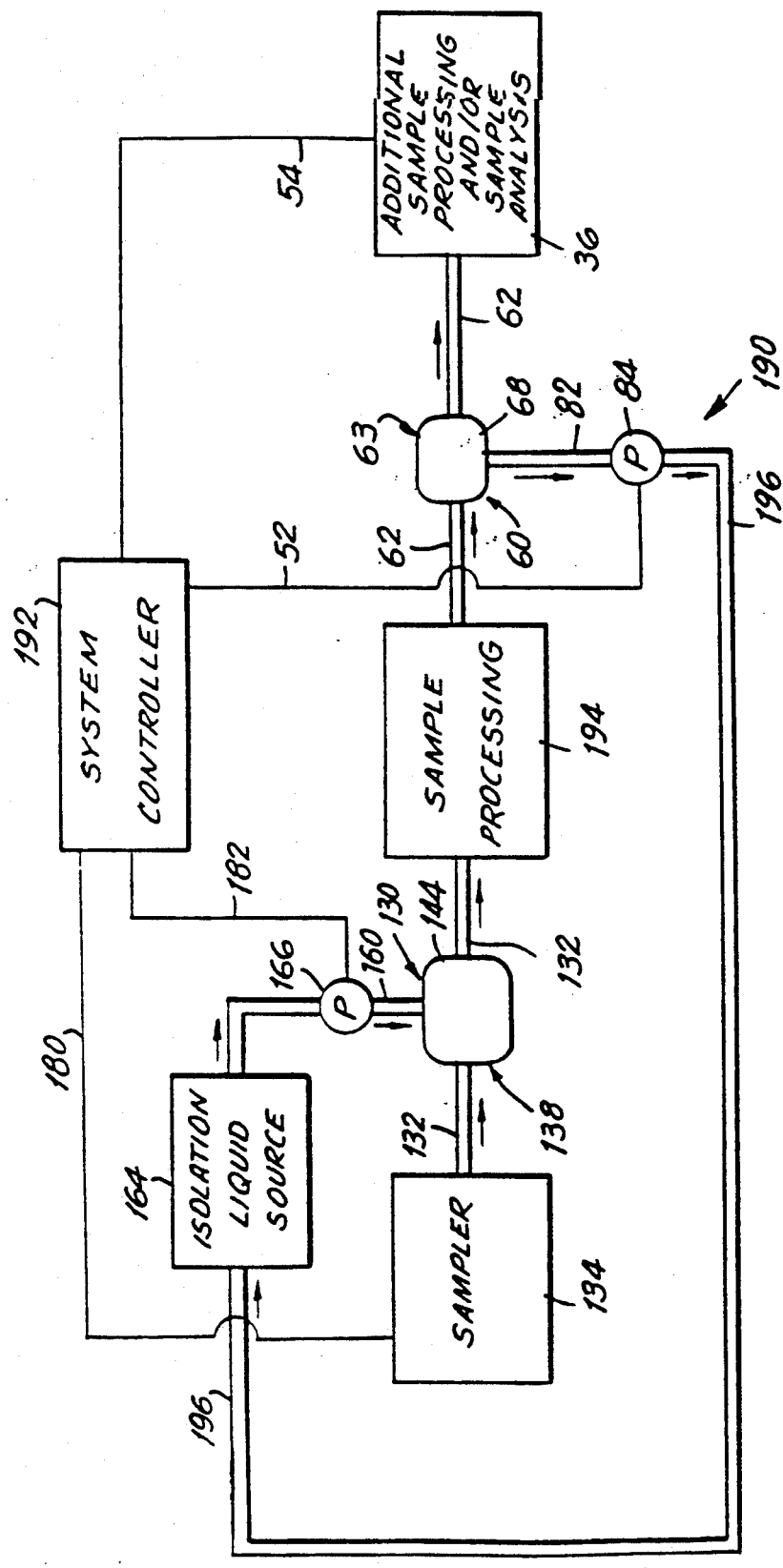
FIG. 7 is an essentially schematic diagram of a continuous flow sample liquid analysis system including the embodiments of the liquid introduction apparatus of our invention of FIG. 6, and the liquid separating apparatus of our invention of FIG. 3.

FIG. 7 illustrates a sample analysis system as generally indicated at 190 and which includes both the liquid introduction apparatus 130 of FIG. 6, and the liquid separation apparatus 60 of FIG. 3. Sampler, isolation liquid source, and additional sample processing and/or sample analysis means, are respectively schematically indicated at 134, 164 and 36; while a system controller is schematically indicated at 192, and is connected as shown by lines 180, 182, 52 and 54 to sampler 134, pump 166, pump 84 and additional sample processing and/or sample analysis means 36 to control and synchronize the respective operations thereof. Sample processing means are indicated schematically at 194, and are operatively disposed as shown between liquid introduction apparatus 130 and liquid separation apparatus 60. A flow conduit 196 is provided as shown in the system of FIG. 7 to connect the outlet of pump 84 to the isolation liquid source 164 to return the separated isolation liquid to the latter.

In the operation of the sample analysis system 190 of FIG. 7, an air-segmented sample liquid stream is supplied from sampler 134 through flow conduit 132 to liquid introduction apparatus 130 for encapsulation of that stream in an isolation liquid layer 18 as described in detail hereinabove with regard to FIG. 6. This stream then flows as indicated to and through sample processing means 194 for processing as required, and therefrom as indicated to and through liquid separation apparatus 60 for removal of the isolation liquid layer therefrom as described in detail hereinabove with regard to FIG. 3, with the thusly removed isolation liquid being returned as indicated from pump 84 through conduit 196 to isolation liquid source 164 for continuous re-use in the system 190. The resultant, substantially isolation liquid-free, air-segmented sample liquid stream is then flowed as indicated through conduit 62 to additional sample processing and/or sample analysis means 36 to those purposes.

Under the above circumstances, it will be clear that the sample analysis system 190 of FIG. 7 provides the particularly significant combined advantages of precise isolation liquid layer formation for maximal sample liquid carryover prevention, and highly effective removal of that isolation liquid layer prior to additional sample liquid processing and/or analysis to maximize the effectiveness and accuracy of the same. In fact, since encapsulation of the air-segmented sample liquid stream by the apparatus 130 is essentially limited to the formation of the isolation liquid layer 18 at the inner wall of flow conduit 132, and since apparatus 60 are effective to remove substantially all of that isolation liquid layer, it will be clear that the air-segmented sample liquid stream which is flowed as described from apparatus 60 to additional sample processing and/or sample analysis means 36 through flow conduit 62 in FIG. 6 will be virtually isolation liquid-free. Too, since the system 190 functions to constantly recirculate and re-use essentially the same isolation liquid, it will be clear that maximum economy of isolation liquid utilization is, of course, achieved.

Although representatively depicted and described as utilizing the apparatus 130 of FIG. 6 for formation of the isolation liquid encapsulated, air-segmented sample liquid stream, and the apparatus 60 of FIG. 3. for the separation of the isolation liquid from that sample liquid stream, it will be immediately clear to those skilled in this art that the sample analysis system 190 of FIG. 7 could alternatively utilize the apparatus 90 of FIG. 5 for isolation liquid encapsulated sample liquid stream formation, and/or the apparatus 10 of FIG. 1 for separation of the isolation liquid from that stream.

Although disclosed hereinabove by way of representative examples as operable in conjunction with air-segmented sample liquid streams, it will be clear that the apparatus and method of our invention are by no means limited to use with sample liquids; and that, with the exception of the apparatus 100 of FIG. 5 wherein the expanding meniscuses of the air segments operate as described to displace the isolation liquid to the inner wall 118 of flow conduit 92, the apparatus and method would be operable to equally advantageous effect with non-air segmented continuous liquid streams.

Various changes may of course be made in the herein disclosed preferred embodiments of the apparatus and method of our invention without departing from the spirit and scope thereof as defined by the appended claims.

What is claimed is:

1. In a method for the introduction of a first liquid into a stream of a second liquid which is immiscible therewith and flowing in conduit means, said conduit means having a wall and an inlet end, said conduit means comprising an inner conduit means surface which is selectively wettable by said second liquid to the substantial exclusion of said first liquid, the improvements comprising, the steps of, introducing said first liquid through said conduit means wall into said second liquid stream at a location in said conduit means downstream of said inlet end to form a stream of said first liquid therewithin by displacing said second liquid stream substantially to the inner conduit means surface for retention thereat by the selective wettability thereof by said second liquid to the substantial exclusion of said first liquid, thereby substantially encapsulating said first liquid stream in said second liquid stream for continued common flow thereof through said conduit means.

2. In a method as in claim 1, the improvements further comprising, the steps of, air-segmenting said first liquid prior to the flow thereof into said conduit means.

3. In a method as in claim 1, the improvements further comprising, the introduction of said first liquid into said second liquid stream comprising, the steps of introducing said first liquid into said second liquid stream generally centrally thereof.

4. In a method as in claim 1 wherein, said inner conduit means surface is hydrophobic, said second liquid is an isolation liquid which is preferentially attracted thereto to the substantial exclusion of aqueous liquids, and said first liquid is an aqueous sample liquid which is immiscible with said isolation liquid, the improvements further comprising, the steps of, analyzing said first liquid during the continued flow thereof through said conduit means.

5. In a method for the introduction of a second liquid into a stream of a first liquid which is immiscible therewith and flowing in conduit means, said conduit means having a wall and an inlet end, said conduit means having an inner surface which is selectively wettable by said second liquid to the substantial exclusion of said first liquid, the improvements comprising, the steps of, introducing said second liquid through said conduit means wall into said first liquid stream at a location in said conduit means downstream of said inlet end to displace said first liquid away from said inner conduit means surface and form a stream of said second liquid at said inner conduit means surface which will be retained thereat by the selective wettability of said inner conduit means surface by said second liquid to the substantial exclusion of said first liquid whereby, said second liquid stream will substantially encapsulate said first liquid stream for continued common flow thereof through said conduit means.

6. In a method as in claim 5, the improvements further comprising, the introduction of said second liquid into said first liquid stream comprising, the steps of, introducing said second liquid thereinto substantially at said inner conduit means surface.

7. In a method as in claim 6 wherein said conduit means include a porous conduit means portion at said inner conduit means surface, the improvements further comprising, the introduction of said second liquid into said first liquid stream comprising, the steps of, flowing said second liquid through said porous conduit means portion into said first liquid stream.

8. In a method as in claim 7, the improvements further comprising, the flow of said second liquid through said porous conduit means portion comprising, the steps of, positively pumping said second liquid for flow therethrough.

9. In a method as in claim 5 wherein, said inner conduit means surface is hydrophobic, said second liquid is an isolation liquid which is preferentially attracted thereto to the substantial exclusion of aqueous liquids, and said first liquid is a sample liquid which is immiscible with said isolation liquid, the improvements further comprising, the steps of, analyzing said first liquid during the continued flow thereof through said conduit means.

10. In a method for the analysis of sample liquids by sample liquids analysis apparatus including sampler means, sample liquid analysis means, a source of an isolation liquid which is immiscible with said sample liquids, and conduit means connecting said sampler means to said sample liquids analysis means, said sampler means supplying a stream of successive sample liquids to said conduit means for flow therethrough to said sample liquids analysis means, said flow conduit means comprising an inner surface which is selectively wettable by said isolation liquid to the substantial exclusion of said sample liquids, the improvements comprising, the steps of, introducing said isolation liquid from said isolation liquid source into said sample liquids stream in said conduit means to form a stream of said isolation liquid at said inner conduit means surface to substantially encapsulate said sample liquids stream therein and thereby minimize sample liquids carryover in said conduit means, and subsequently substantially separating said isolation liquid stream from said sample liquids stream downstream in said conduit means prior to the flow of said sample liquids stream to said sample liquids analysis means, whereby interference by said isolation liquid with sample liquids analysis will be minimized.

11. In a method as in claim 10, the improvements further comprising, the steps of, air segmenting said sample liquids stream prior to the introduction of said isolation liquid thereinto.

12. In a method as in claim 10, the improvements further comprising, the steps of, returning the thusly separated isolation liquid to said isolation liquid source for re-use in said sample liquids analysis apparatus.

13. In a method for the substantial separation of at least a portion of one liquid from a common stream of two immiscible liquids flowing in flow conduit means, said conduit means including an inner surface which is selectively wettable by one of said liquids to the substantial exclusion of the other of said liquids, the improvements comprising, the steps of, substantially separating at least said liquid portion from said common liquids stream attendant the flow thereof in said conduit means, and flowing the thusly substantially separated liquid portion out of said conduit means while continuing the flow of the remainder of said common liquids stream through said conduit means.

14. In a method for the introduction of a liquid into a stream of another liquid which is immiscible therewith and flowing in conduit means, said conduit means having a wall and an inlet end, said conduit means including an inner surface which is selectively wettable by one of said liquids to the substantial exclusion of the other of said liquids, the improvements comprising, the steps of, introducing said liquid through said conduit means wall into the stream of said another of said liquids at a location within said conduit means downstream of said inlet end to from a common stream of said liquids therewithin, with said liquid which selectively wets said inner conduit means surface being preferentially attracted thereto to the substantial exclusion of the other of said liquids to form a liquid stream at said inner conduit means surface which substantially encapsulates the stream of the other of said liquids within said conduit means.

15. In a method for the substantial separation of a second liquid from a common stream of said second liquid and a first liquid which is immiscible therewith flowing in conduit means including an inner conduit means surface which is selectively wettable by said second liquid to the substantial exclusion of said first liquid, the improvements comprising, the steps of, substantially separating said second liquid from said common stream of said first and second immiscible liquids attendant the flow thereof in said conduit means, and flowing the thusly substantially separated second liquid out of said conduit means while continuing the flow of the remainder of said common liquids stream in said conduit means, and wherein said second liquid is flowing primarily at said inner conduit means surface is substantial contact therewith, and said first liquid is flowing primarily within said second liquid substantially out of contact with said said conduit means inner surface, the step of substantially separating said second liquid from said common stream comprising, substantially separating said second liquid from said common liquids stream generally at said inner conduit means surface.

16. In a method for substantially separating at least a portion of a first liquid from a common liquids stream of first and second immiscible liquids flowing in conduit means including an inner conduit means surface which is selectively wettable by said second liquid to the substantial exclusion of said first liquid, the improvements comprising, the steps of, substantially separating at least a portion of said first liquid from said common stream of said first and second liquids attendant the flow thereof in said conduit means, and flowing the thusly substantially separated first liquid portion out of said conduit means while continuing the flow of the remainder of said common liquids stream through said conduit means, and wherein said second liquid is flowing primarily at said inner conduit means surface in substantial contact therewith, and said first liquid is flowing primarily within said second liquid substantially out of contact with aid inner conduit means surface, the step of, substantially separating at least a portion of said first liquid from said common liquids stream comprising, substantially separating said first liquid portion from the generally central region of said common liquids stream in said conduit means, and wherein said inner conduit means surface is hydrophobic, said second liquid is an isolation liquid which is preferentially attracted thereto to the substantial exclusion of aqueous liquids, and said first liquid is an aqueous sample liquid which is immiscible with said isolation liquid, the improvements further comprising, the steps of, analyzing the thusly separated portion of said first liquid.

17. In a method for substantially separating at least a portion of a first liquid from a common liquids stream of first and second immiscible liquids flowing in conduit means including an inner conduit means surface which is selectively wettable by said second liquid to the substantial exclusion of said first liquid, the improvements comprising, the steps of, substantially separating at least a portion of said first liquid from said common stream of said first and second liquids attendant the flow thereof in said conduit means, and flowing the thusly substantially separated first liquid portion out of said conduit means while continuing the flow of the remainder of said common liquids stream through said conduit means, and wherein said second liquid is flowing primarily at said inner conduit means surface in substantial contact therewith, and said first liquid is flowing primarily within said second liquid substantially out of contact with said inner conduit means surface, the step of substantially separating at least a portion of said first liquid from said common liquids stream comprising, substantially separating said first liquid portion from the generally central region of said common liquids stream in said conduit means, and wherein said common liquids stream is air-segmented, the steps of, separating portions of said air segments in said common liquids stream therefrom attendant the substantial separation of said first liquid portion, and air-segmenting said substantially separated first liquid portion with the thusly separated air segment portion.

18. In a method for the substantial separation of a second liquid from a common stream of said second liquid and a first liquid which is immiscible therewith and flowing in conduit means including an inner surface which is selectively wettable by said second liquid to the substantial exclusion of said first liquid, the improvements comprising, the steps of, substantially separating said second liquid from said common stream of said first and second immiscible liquids attendant the flow thereof in said conduit means, and flowing the thusly substantially separated second liquid out of said conduit means while continuing the flow of the remainder of said common liquids stream in said conduit means and wherein, said second liquid is flowing primarily at said inner conduit means surface in substantial contact therewith, and said first liquid is flowing primarily within said second liquid substantially out of contact with said conduit means inner surface, the step of substantially separating said second liquid from said common stream comprising, substantially separating said second liquid from said common liquids stream generally at said inner conduit means surface, said flow conduit means including a porous conduit means portion at the inner conduit means surface, and the substantial separation of said second liquid from said common liquids stream and flow thereof out of said conduit means comprising, the steps of flowing said second liquid through said porous conduit means portion out of said conduit means.

* * * * *